US008236992B2

(12) United States Patent
Masson et al.

(10) Patent No.: US 8,236,992 B2
(45) Date of Patent: Aug. 7, 2012

(54) PREPARATION OF PURIFIED HYDROQUINONE

(75) Inventors: Jean-Claude Masson, Lyons (FR); Philippe Carvin, Lyons (FR); Jean-Louis Grieneisen, Corbas (FR)

(73) Assignee: Rhodia Operations, Aubervilliers (FR)

( * ) Notice: Subject to any disclaimer, the term of this patent is extended or adjusted under 35 U.S.C. 154(b) by 544 days.

(21) Appl. No.: 12/306,765

(22) PCT Filed: Jun. 27, 2007

(86) PCT No.: PCT/FR2007/001081
§ 371 (c)(1),
(2), (4) Date: Nov. 13, 2009

(87) PCT Pub. No.: WO2008/000957
PCT Pub. Date: Jan. 3, 2008

(65) Prior Publication Data
US 2010/0069682 A1    Mar. 18, 2010

(30) Foreign Application Priority Data
Jun. 29, 2006    (FR) ..................................... 06 05872

(51) Int. Cl.
*C07C 37/84* (2006.01)
(52) U.S. Cl. ......... 568/750; 568/751; 568/752; 568/753
(58) Field of Classification Search .................. 568/750, 568/751, 752, 753
See application file for complete search history.

(56) References Cited

U.S. PATENT DOCUMENTS

| 1,908,817 | A | * | 5/1933 | Britton et al. ................. 568/750 |
| 3,884,983 | A | * | 5/1975 | Burkholder et al. .......... 568/753 |
| 3,900,523 | A | * | 8/1975 | Tada et al. ..................... 568/753 |
| 3,929,910 | A | * | 12/1975 | Suda et al. ..................... 568/751 |
| 3,969,420 | A | * | 7/1976 | Suda et al. ..................... 568/751 |
| 4,119,791 | A | * | 10/1978 | Hollingshead et al. ....... 568/768 |
| 4,308,110 | A |   | 12/1981 | Hosaka et al. |
| 4,424,381 | A | * | 1/1984 | Leston .......................... 568/753 |

FOREIGN PATENT DOCUMENTS

FR    2 467 185    4/1981

OTHER PUBLICATIONS

Puel et al., "Simulation and analysis of industrial crystallization processes through multidimensional population balance equations, Part 2: a study of semi-batch crystallization", Chem. Eng. Science, 2003, pp. 3729-3740, vol. 58, No. 16, Elsevier Ltd.
International Search Report corresponding to PCT/FR 2007/001081, issued on Mar. 6, 2008.

* cited by examiner

*Primary Examiner* — Brian J Davis
(74) *Attorney, Agent, or Firm* — SNR Denton US LLP (57) ABSTRACT

Hydroquinone devoid of impurities is prepared from a crude hydroquinone essentially containing hydroquinone and small amounts of impurities including at least resorcinol, pyrogallol and traces of pyrocatechol and comprises at least the following steps: dissolving the crude hydroquinone in water, crystallizing the hydroquinone, separating the purified hydroquinone, and, optionally, drying the purified hydroquinone.

30 Claims, 4 Drawing Sheets

PREPARATION OF PURIFIED HYDROQUINONE

CROSS-REFERENCE TO PRIORITY/PCT APPLICATIONS

This application claims priority under 35 U.S.C. §119 of FR 0605872, filed Jun. 29, 2006, and is a continuation/national phase of PCT/FR 2007/001081, filed Jun. 27, 2007 and designating the United States (published in the French language on Jan. 3, 2008, as WO 2008/000957 A2; the title and abstract were also published in English), each hereby expressly incorporated by reference in its entirety and each assigned to the assignee hereof.

A subject matter of the present invention is a process for the preparation of purified hydroquinone.

The invention is targeted at providing hydroquinone freed from the impurities resulting from its process of preparation.

According to one embodiment, the invention provides a process which makes it possible to obtain hydroquinone of high purity.

Hydroquinone (or 1,4-dihydroxybenzene) is a product widely used in numerous fields of application as polymerization inhibitor or antioxidant in elastomers or as synthetic intermediate. Another field of application is photography. It follows that this is a staple.

Varying purities are required according to the markets concerned.

This is because, if some applications, in particular photography, require a very high degree of purity, others are satisfied with a technical hydroquinone, that is to say a hydroquinone having a lower degree of purity, in order to minimize the operating costs.

Thus, hydroquinone has to satisfy variable purity requirements which can in some cases be fairly restrictive.

The problem which is posed is that hydroquinone is not easy to purify as it is an oxidation-sensitive product which quickly results in decomposition products which are colored.

Furthermore, pyrogallol is coproduced, admittedly in low amounts, with hydroquinone. In point of fact, this compound very quickly decomposes thermally and results in colored impurities which it is also necessary to remove.

Furthermore, different physicochemical characteristics, in terms of particle size, flowability or rate of dissolution, may be required depending on the applications.

Thus, the market requires diversified products having a good chemical stability on storage.

One of the synthetic routes to hydroquinone consists in carrying out hydroxylation of phenol by hydrogen peroxide, in particular in the presence of homogeneous or heterogeneous acid catalysts.

Thus, recourse may be had, as according to FR 2 071 464, to a strong protic acid, that is to say an acid exhibiting a pKa in water of less than 0.1, preferably of less than −1.

Mention may be made, as examples of strong protic acids, inter alia, of sulfuric acid, hydrochloric/sulfuric acid mixture, perchloric acid or sulfonic acids, such as, for example, methanesulfonic, trifluoromethanesulfonic, toluenesulfonic or phenolsulfonic acid.

Mention may be made, as other examples of protic acid catalysts, of sulfonic resins and more particularly resins sold under various trade names. Mention may be made, inter alia, of the following resins: TEMEX™ 50, AMBERLYST™ 15, AMBERLYST™ 35, AMBERLYST™ 36 and DOWEX™ 50W.

The abovementioned resins are composed of a polystyrene backbone which carries functional groups which are sulfonic groups. The polystyrene backbone is obtained by polymerization of styrene and divinylbenzene under the influence of an activation catalyst, generally an organic peroxide, which results in a crosslinked polystyrene which is subsequently treated with concentrated sulfuric or hydrochloric/sulfuric acid, resulting in a sulfonated styrene/divinylbenzene copolymer.

It is also possible to resort to sulfonic resins which are phenol/formaldehyde copolymers and which carry, on the aromatic ring, a methylenesulfonic group, for example the resin sold under the name DUOLITE™ Arc 9359.

Other commercially available resins are also suitable and mention may be made of perfluorinated resins carrying sulfonic groups and more particularly Nafion, which is a copolymer of tetrafluoroethylene and of perfluoro[2-(fluoroslfonylethoxy)propyl] vinyl ether.

Mention may be made, as other catalysts suitable in hydroxylation processes, of iron(II) and copper(II) complexes (FR 2 121 000, USSR 1 502 559) and any other catalyst of Fenton type.

Other processes for the preparation of hydroquinone involve heterogeneous catalysis. Thus, it is possible to employ an acid zeolite of titanium silicalite (or titanosilicalite-1) type or of iron silicalite type of TS-1 type (FR 2 489 816), a zeolite of MEL titanium silicalite type (EP 1 131 264) or a titanozeosilite of MFI type (EP 1 123 159). It is also possible to use an MCM-22 zeolite (FR 2 856 681).

On conclusion of such hydroxylation reactions, a mixture is obtained essentially comprising pyrocatechol (or 1,2-dihydroxybenzene) and hydroquinone in variable proportions, generally with a pyrocatechol/hydroquinone ratio by weight of the order of 0.25 to 4.0, and also various byproducts in much smaller amounts, in particular resorcinol (or 1,3-dihydroxybenzene) and pyrogallol (or 1,2,3-trihydroxybenzene), generally at contents of the order of 0.5 to 4.0% by weight, percentages expressed with respect to the amount of hydroquinone and of pyrocatechol formed.

Mixtures with variable compositions, comprising, by weight, from 20 to 80% of pyrocatechol, from 80 to 20% of hydroquinone, from 0.1 to 2% of resorcinol and from 0.1 to 2% of pyrogallol, are obtained.

Typically, mixtures comprising, by weight, from 50 to 80% of pyrocatechol, from 20 to 50% of hydroquinone, from 0.1 to 2% of resorcinol and from 0.1 to 2% of pyrogallol are obtained.

In order to isolate the hydroquinone from crude mixtures of this type, one currently known method consists in distilling said mixture, making it possible to obtain, at the distillation top, pyrocatechol (which is the most volatile compound of the mixture) and, at the distillation bottom, a "crude hydroquinone", namely a mixture essentially comprising hydroquinone in combination with small amounts of impurities (in particular resorcinol and pyrogallol, and also possible traces of pyrocatechol not removed by the distillation).

The invention provides a process which makes it possible, starting from crude hydroquinone, to obtain a hydroquinone having the desired purity.

Thus, the object of the invention is to provide a flexible process which makes it possible to control the purity of the desired hydroquinone and to obtain a product which can meet high-purity requirements.

In accordance with the process of the invention and according to the chosen embodiment capable of comprising a different sequence of the stages, it is possible to vary the purity of the product obtained.

There has now been found, and it is this which constitutes the subject matter of the present invention, a process for the preparation of purified hydroquinone starting from a crude hydroquinone $HQ^0$ essentially comprising hydroquinone and low amounts of impurities, including at least resorcinol, pyrogallol and traces of pyrocatechol, characterized in that it comprises at least the following stages: dissolution of the crude hydroquinone in water, crystallization of the hydroquinone, separation of the purified hydroquinone and optionally a stage of drying the purified hydroquinone.

Thus, according to the invention, a hydroquinone is obtained which has a purity more or less improved according to the type of embodiments of the invention.

The exact composition of the crude hydroquinone $HQ^0$ treated according to the stages of the process of the invention can vary to a fairly large extent, the process of the invention proving, however, to be especially advantageous for crude hydroquinones essentially comprising hydroquinone in a proportion of at least 90% by weight (preferably of at least 91% by weight) and small amounts of impurities of less than 10% by weight (preferably of less than 9% by weight). The major impurities are resorcinol and pyrogallol, pyrocatechol representing less than 1% of the weight of impurities. The pyrogallol/resorcinol ratio by weight generally varies between 0.2 and 5.

The process of the invention is particularly advantageous in treating crude hydroquinones comprising hydroquinone in a proportion of 96 to 99.5% by weight and contents of impurities of the order of 0.5 to 4% by weight, for example of 0.5 to 2% by weight, in particular of 1 to 2% by weight, with respect to the total weight of the crude hydroquinone.

Typically, a crude hydroquinone $HQ^0$ treated according to the invention comprises from 0.1 to 2% by weight, for example from 0.2 to 1% by weight, of light impurities essentially composed of hydroquinone isomers, namely resorcinol and residual pyrocatechol. Resorcinol is generally a predominant impurity within the light impurities, light impurities generally comprising at least 50% by weight of resorcinol, with respect to the total weight of the light impurities, for example at least 70% by weight, in particular at least 80% by weight, especially at least 90% by weight, indeed even more. In addition to the resorcinol, the light impurities present in the crude hydroquinone $HQ^0$ can in particular comprise pyrocatechol.

Furthermore, in the crude hydroquinone $HQ^0$, the amount of heavy impurities, the most important of which is composed of pyrogallol, is usually from 0.1 to 2% by weight, for example from 0.2 to 1% by weight. These heavy impurities include in particular pyrogallol, generally as predominant heavy impurity, generally in combination with other heavy impurities, in particular tars or alternatively products from a thermal decomposition of hydroquinone, such as quinones. Thus, the heavy impurities generally comprise at least 50% by weight of pyrogallol, with respect to the total weight of the heavy impurities, for example at least 70% by weight, indeed even at least 80% by weight, in particular at least 90% by weight or more.

According to a specific embodiment, the crude hydroquinone $HQ^0$ treated according to the process of the invention is obtained, or capable of being obtained, from a reaction mixture resulting from the hydroxylation of phenol by hydrogen peroxide in the presence of acid catalysts of the type mentioned above in the present description, after substantial removal of the pyrocatechol by distillation.

A crude hydroquinone $HQ^0$ suited to the process of the invention comprises, by weight with respect to the total amount of crude hydroquinone:
  from 96 to 99.5% of hydroquinone,
  from 0.1 to 2%, preferably from 0.2 to 1%, of resorcinol,
  from 0.1 to 2%, preferably from 0.2 to 1%, of pyrogallol,
  optionally pyrocatechol in the form of traces, typically at a content of less than 500 ppm (0.05%), preferably of less than 100 ppm (0.01%).

Whatever the exact nature of the crude hydroquinone $HQ^0$ treated according to the process of the invention, the stages of the process of the invention are advantageously carried out under the conditions set out below.

In order to facilitate understanding of embodiments of the processes of the invention, FIGS. 1 to 4, which diagrammatically represent the various alternative forms of the process of the invention, are given below without, however, binding the scope of the invention to these.

FIRST EMBODIMENT

Figure 1:
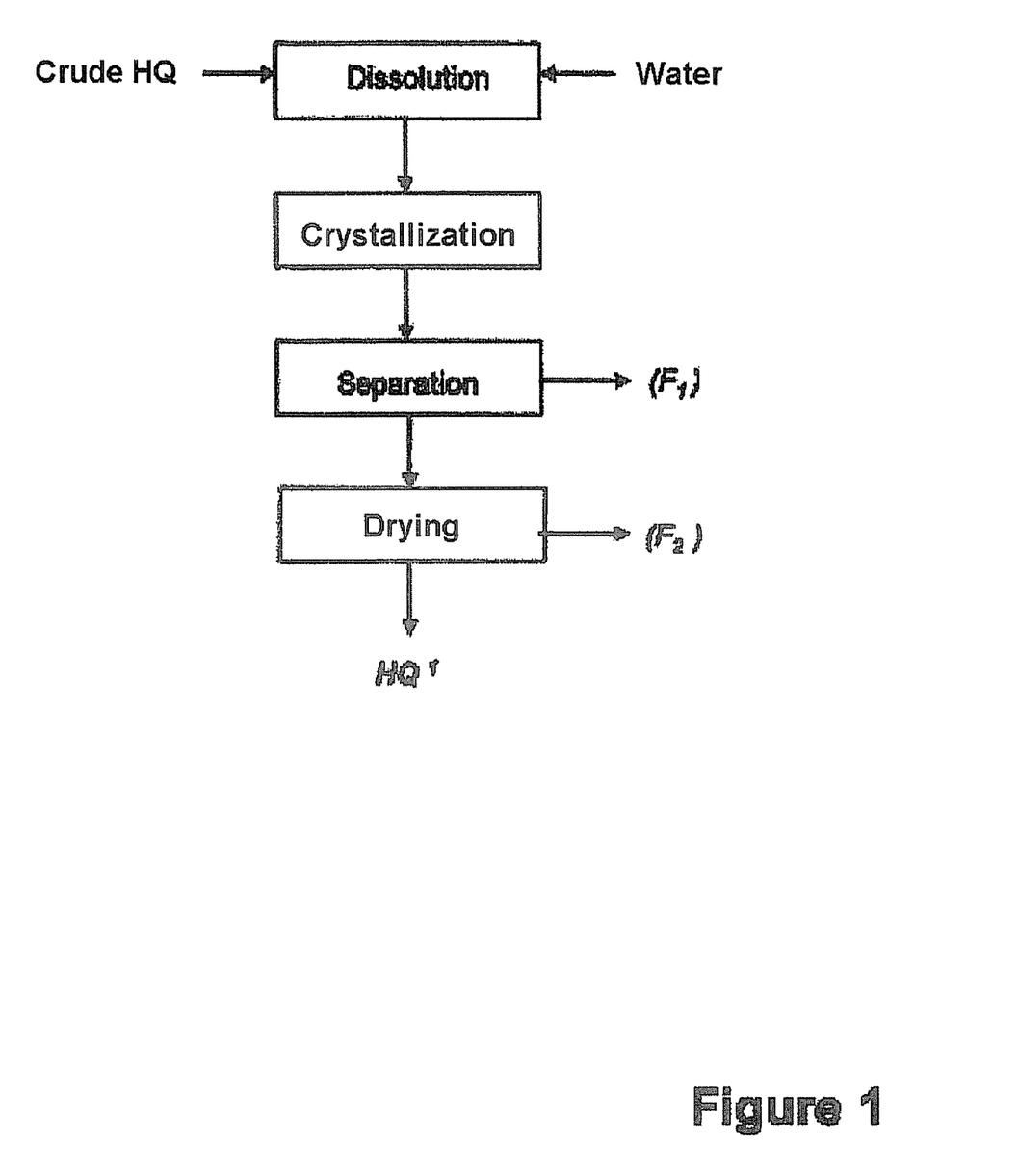
FIG. 1 illustrates steps of a first embodiment of a process for the purification of hydroquinones which comprises the steps of dissolving the hydroquinone in water, crystallizing the hydroquinone, separating the crystalline hydroquinone from an aqueous phase composed of the crystallization aqueous mother liquors and drying the crystalline hydroquinone.

Represented in FIG. 1

In accordance with the process of the invention the hydroquinone is first dissolved in water, followed by a crystallization, a solid/liquid separation and a drying.

More specifically, the process comprises the following stages:
  dissolution of the crude hydroquinone in water,
  crystallization of the hydroquinone,
  solid/liquid separation, making it possible to separate the crystalline hydroquinone from an aqueous phase composed of the crystallization aqueous mother liquors ($F_1$),
  drying of the washed hydroquinone with removal of water ($F_2$).

This final stage is optional but generally the hydroquinone is sold in a dry form.

The hydroquinone and the water are introduced into a stirred reactor, the temperature of which can be controlled either using a heat exchanger or by circulation of heat-exchange fluid in a jacket with which it would be provided.

Mention may be made, as heat-exchange fluids suitable for the invention, in particular of water or else an organic solvent, such as chosen from heavy esters of carboxylic acids (for example, octyl phthalate), aromatic ethers, such as diphenyl ether and/or benzyl ether, biphenyl, terphenyls, the other optionally partially hydrogenated polyphenyls, paraffinic and/or naphthenic oils, petroleum distillation residues, and the like.

The amount of water introduced in order to bring about the dissolution of the hydroquinone is such that the concentration of the hydroquinone in the water is between 20 and 50% by weight and preferably between 20 and 40% by weight.

The dissolution operation is preferably carried out at a temperature ranging from 70° C. to 100° C.

The various parameters can be adjusted and the concentration can be increased as the temperature chosen increases.

In a following stage, the hydroquinone is crystallized by cooling from the dissolution temperature down to a lower temperature of between 0 and 40° C., preferably between 5 and 25° C.

Crystallization is carried out in the appliances conventionally used, such as in stirred reactors (known as crystallizers) with internal exchangers and/or circulation of heat-exchange fluid in a jacket. Cooling can also be carried out by partial evaporation of the solvent (water) under reduced pressure (15 mbar and 250 mbar) and with optionally recycling of the condensates.

The operation generally lasts between 60 and 720 min and depends on the method of crystallization, the size of the crystallizers and the feed charges or flow rates.

The size of the crystals and the length to width elongation factor are controlled by varying in particular the following parameters: cooling temperature profile, power of the stirring and residence time in the crystallizer.

The stirring is defined by the power dissipated, which is preferably between 0.4 and 1.2 kilowatt/m$^3$ of reactor volume.

It is also possible to control the particle size of the product obtained by introducing crystallization seeds at a content preferably of less than 2%. Use is made, as crystallization seeds, of a small amount of crystalline hydroquinone originating from a preceding manufacture and of appropriate particle size.

At the end of the operation, a hydroquinone suspension is obtained.

The crystalline product is subsequently separated according to conventional solid/liquid separation techniques, preferably by filtration, centrifuging or draining.

The separation operation is generally carried out at the temperature of the end of crystallization; however, a different temperature can be chosen.

A solid is recovered which is essentially purified hydroquinone comprising from 5 to 20% of water, preferably 5 to 10% of water, depending on the separation technique used, and an aqueous phase is recovered which is composed of the crystallization aqueous mother liquors ($F_1$) essentially comprising water and hydroquinone at a content generally of less than approximately 10% by weight, preferably of less than 7% by weight.

It should be noted that the dissolution and crystallization operations can be carried out continuously or batchwise.

According to a continuous implementation, it is possible to provide a cascade of stirred reactors and crystallizers in series or in parallel with temperatures which can be different but chosen within the predefined region.

As mentioned above, it is possible to subject the recovered hydroquinone to a drying operation.

The drying temperature is advantageously chosen between 100° C. and 140° C.

Drying is carried out according to techniques well known to a person skilled in the art and in conventionally used appliances, such as driers by contact at atmospheric pressure or under reduced pressure, air convection driers (pneumatic drier type) or an inert gas, preferably nitrogen, with the possibility of recycling inert gas. The hydroquinone can also be dried according to the fluidized bed technique.

Following the drying, a stream ($F_2$), composed essentially of water, and the dried product, namely the hydroquinone $HQ^1$, are obtained, the characteristics of the hydroquinone $HQ^1$ being as follows:
  the hydroquinone content is greater than or equal to 98.5%,
  the resorcinol content is less than 4000 ppm,
  the pyrogallol content is less than 4000 ppm,
  the coloring is less than 500 Hazen.

The contents of diphenols and pyrogallol are determined by high performance liquid chromatography.

The coloring is determined at ambient temperature by spectrocolorimetry on an aqueous solution of hydroquinone at 5% by weight in distilled water.

According to the embodiment illustrated in FIG. 1, the content of hydroquinone obtained is less than or equal to 99.2% approximately.

SECOND EMBODIMENT

Figure 2:
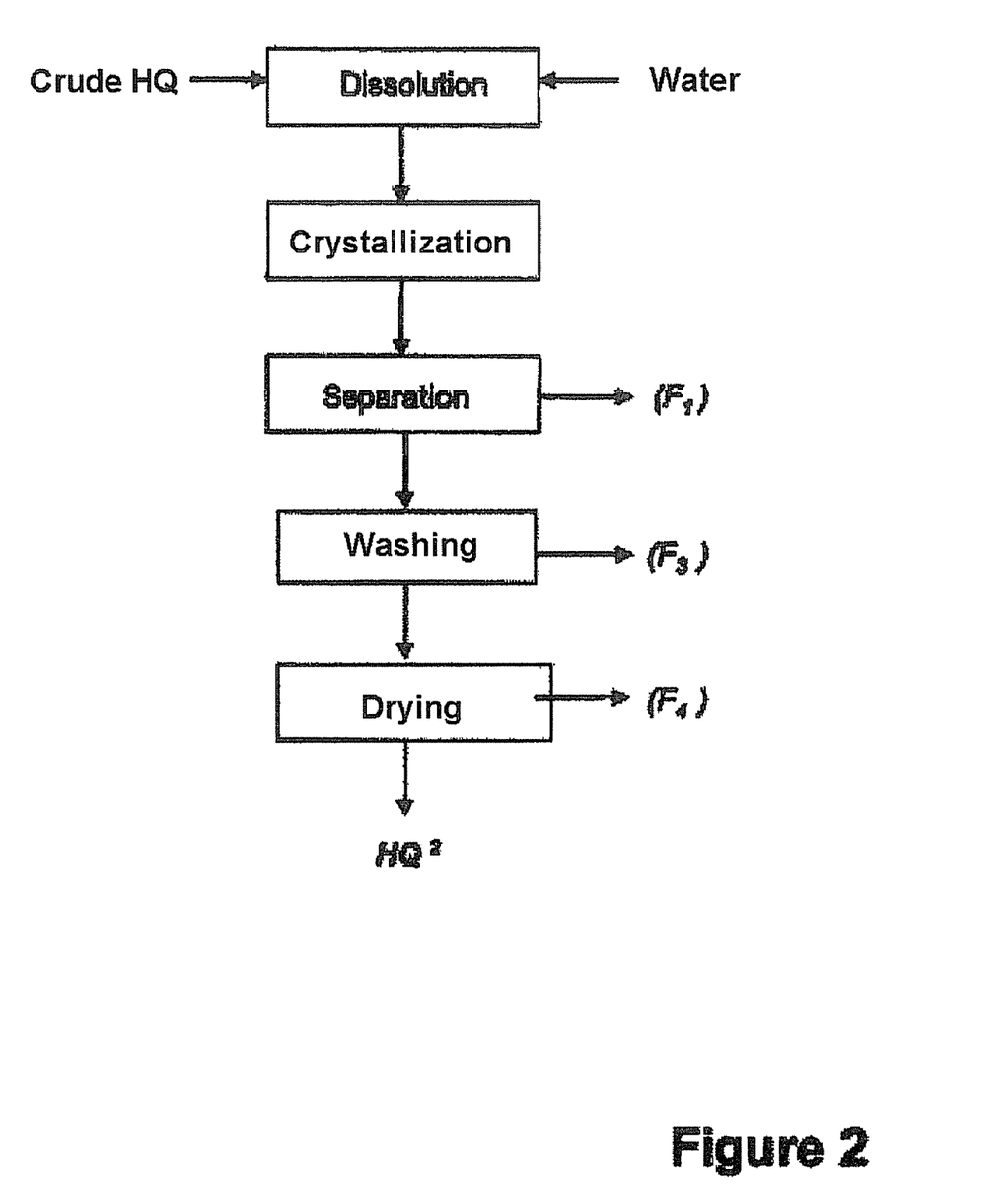
FIG. 2 illustrates steps of a second embodiment of a process for the purification of hydroquinones which further comprises the additional step of washing the separated crystalline hydroquinone after separating the crystalline hydroquinone from an aqueous phase composed of the crystallization aqueous mother liquors.

Represented in FIG. 2

In accordance with the process of the invention, a purer hydroquinone with respect to $HQ^2$ is obtained by carrying out an additional stage.

Thus, the process of the invention, according to this embodiment, comprises the dissolution of hydroquinone in water, followed by a crystallization, a solid/liquid separation, a washing and a drying.

More specifically, the process comprises the following stages:
  dissolution of the crude hydroquinone in water,
  crystallization of the hydroquinone,
  solid/liquid separation, making it possible to separate the crystalline hydroquinone from an aqueous phase composed of the crystallization aqueous mother liquors ($F_1$),
  washing the separated hydroquinone, making it possible to collect aqueous wash liquors ($F_3$),
  drying the washed hydroquinone with removal of water ($F_4$).

The dissolution of the hydroquinone in the water, the crystallization and the separation are carried out as described above but subsequently the separated hydroquinone is washed, before an optional drying.

The washing operation is carried out while employing an amount of water ranging from 20 to 60% of the weight of hydroquinone. The washing operation can be carried out in one or more installments.

The washing operation can be carried out on the same solid/liquid separation apparatus, i.e. on a filter, on an extractor or in the centrifuge, or else according to a reslurrying operation which consists in recovering the hydroquinone and introducing it into another reactor with water and in then separating the washed hydroquinone.

At the end of the operation, the aqueous wash liquors ($F_3$), predominantly comprising water and to a minor extent (less than 10% by weight) hydroquinone and impurities, are collected.

The washed hydroquinone is subjected to a drying operation as described above.

Subsequent to the drying operation, a stream ($F_4$) is obtained which is essentially composed of water and a dried product, namely the hydroquinone $HQ^2$, is obtained, the characteristics of which are as follows:
  the hydroquinone content is greater than or equal to 99.5%,
  the resorcinol content is less than 500 ppm, the pyrogallol content is less than 100 ppm,
the coloring is less than 30 Hazen.

According to the embodiment illustrated in FIG. 2, the content of hydroquinone obtained is less than or equal to 99.9% approximately.

THIRD EMBODIMENT

Figure 3:
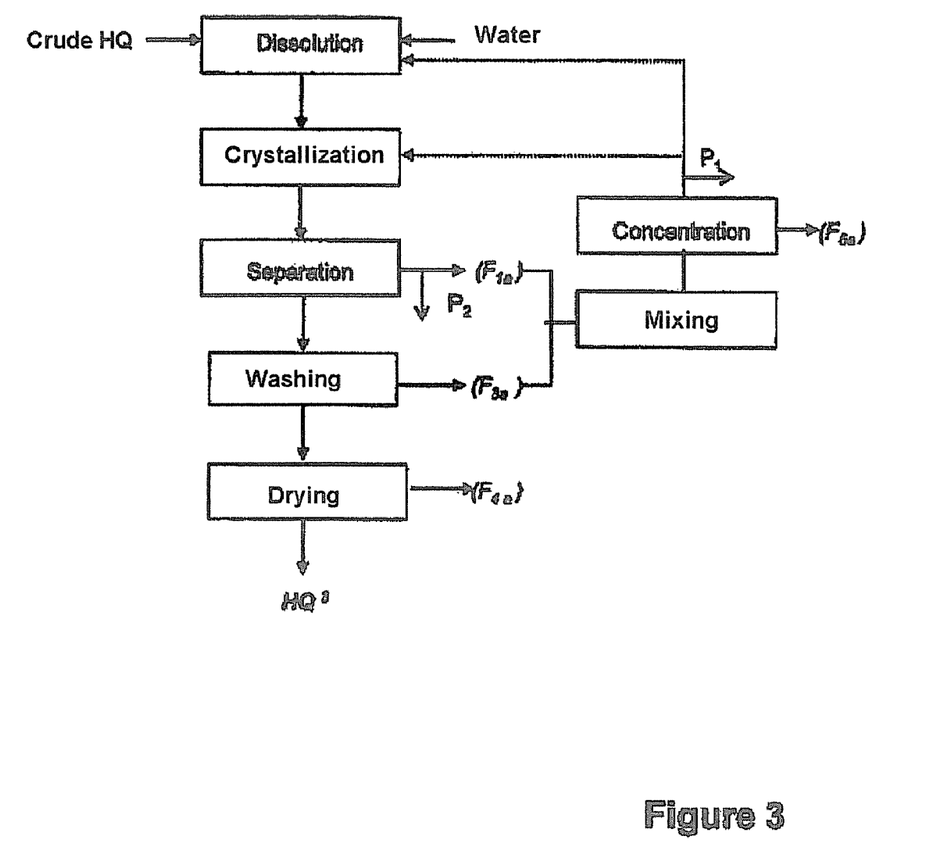
FIG. 3 illustrates steps of a third embodiment of a process for the purification of hydroquinones which comprises the additional steps of mixing and concentrating washings mother liquors from various steps.

Represented in FIG. 3

In accordance with the process of the invention, a hydroquinone $HQ^3$ of different quality is obtained according to a process comprising the following stages:
dissolution of the crude hydroquinone in water,
crystallization of hydroquinone,
solid/liquid separation, making it possible to separate the crystalline hydroquinone from an aqueous phase composed of the crystallization aqueous mother liquors $(F_{1a})$,
washing the separated hydroquinone, making it possible to collect aqueous wash liquors $(F_{3a})$,
drying the washed hydroquinone with removal of water $(F_{4a})$,
mixing the recovered streams $(F_{1a})$ and $(F_{3a})$,
concentrating the mixture obtained,
and recycling the latter to the dissolution or crystallization stage.

According to this alternative form of the process of the invention, the stages described above are repeated and the aqueous phase $(F_{1a})$ obtained subsequent to the separation operation is mixed with the aqueous wash liquors recovered $(F_{3a})$.

This operation is carried out in any stirred reactor.

The mixing is carried out at a temperature advantageously chosen between 5° C. and 70° C.

According to one characteristic of the process of the invention, the mixture obtained can be concentrated so as to increase the concentration of hydroquinone in the medium from 5% by weight to 40% by weight, preferably from 7% to 35%.

Thus, during this operation, a stream $(F_{5a})$ comprising water (for example, from 70 to 90% by weight, with respect to the weight of the reaction medium resulting from the mixing operation) is removed.

A first method consists, while remaining within the above-mentioned temperature region, in reducing the reaction pressure, by reduction in pressure. This reduction in pressure is carried out so as to remove, at the top, the amount of water necessary to achieve, in the reaction medium, the target concentration of hydroquinone.

The desired concentration of hydroquinone is obtained by removing water and volatile impurities.

Another embodiment for concentrating the reaction medium consists in distilling off the amount of a portion of the water to achieve, in the reaction medium, the desired concentration of hydroquinone.

The distillation can be carried out at atmospheric pressure at a temperature of the order of 100° C.

The distillation can also be carried out under a pressure slightly below atmospheric pressure, for example from 200 to 750 mm of mercury, and at a temperature of less than 100° C. Generally, the pressure is chosen in order to have a distillation temperature lying between 70° C. and 100° C.

The distillation can optionally be carried out under pressure greater than atmospheric pressure.

These operations are carried out in conventional appliances, such as distillation columns or standard evaporators under pressure.

This concentrated stream is advantageously recycled, either to the dissolution stage or to the crystallization feed.

In order to minimize the impurities present in this recirculation loop, it is preferable to carry out a bleeding or several bleedings of one of the streams comprising the impurities.

The bleeding consists in withdrawing a fraction of said stream. It is determined so that the overall loss of hydroquinone, with respect to the crude hydroquinone, is preferably between 0.5 and 2% by weight.

It can be carried out at $(P_1)$, preferably at the outlet of the concentrating region. It is carried out via a valve placed on the line conveying the concentrated stream, at the outlet of the concentrating operation but before recycling.

It is also possible to carry out a bleeding at $(P_2)$ on the stream composed of the aqueous phase $(F_{1a})$ resulting from the separation of the hydroquinone after crystallization but before mixing with the stream $(F_{3a})$ composed of the aqueous wash liquors.

It is preferable to carry out the purging at the outlet of the concentrating region.

The bleeding can be carried out continuously or noncontinuously.

The control of the bleeding makes it possible to adjust the chemical purity of the hydroquinone obtained and also of the overall yield of the process.

Following the various operations defined according to the scheme illustrated in FIG. 3, hydroquinone $HQ^3$ is obtained, the characteristics of which are as follows:
the hydroquinone content is greater than or equal to 99%,
the resorcinol content is less than 5000 ppm,
the pyrogallol content is less than 200 ppm,
the coloring is less than 50 Hazen.

According to the embodiment illustrated in FIG. 3, the content of hydroquinone obtained is less than or equal to 99.5% approximately.

FOURTH EMBODIMENT

Figure 4:
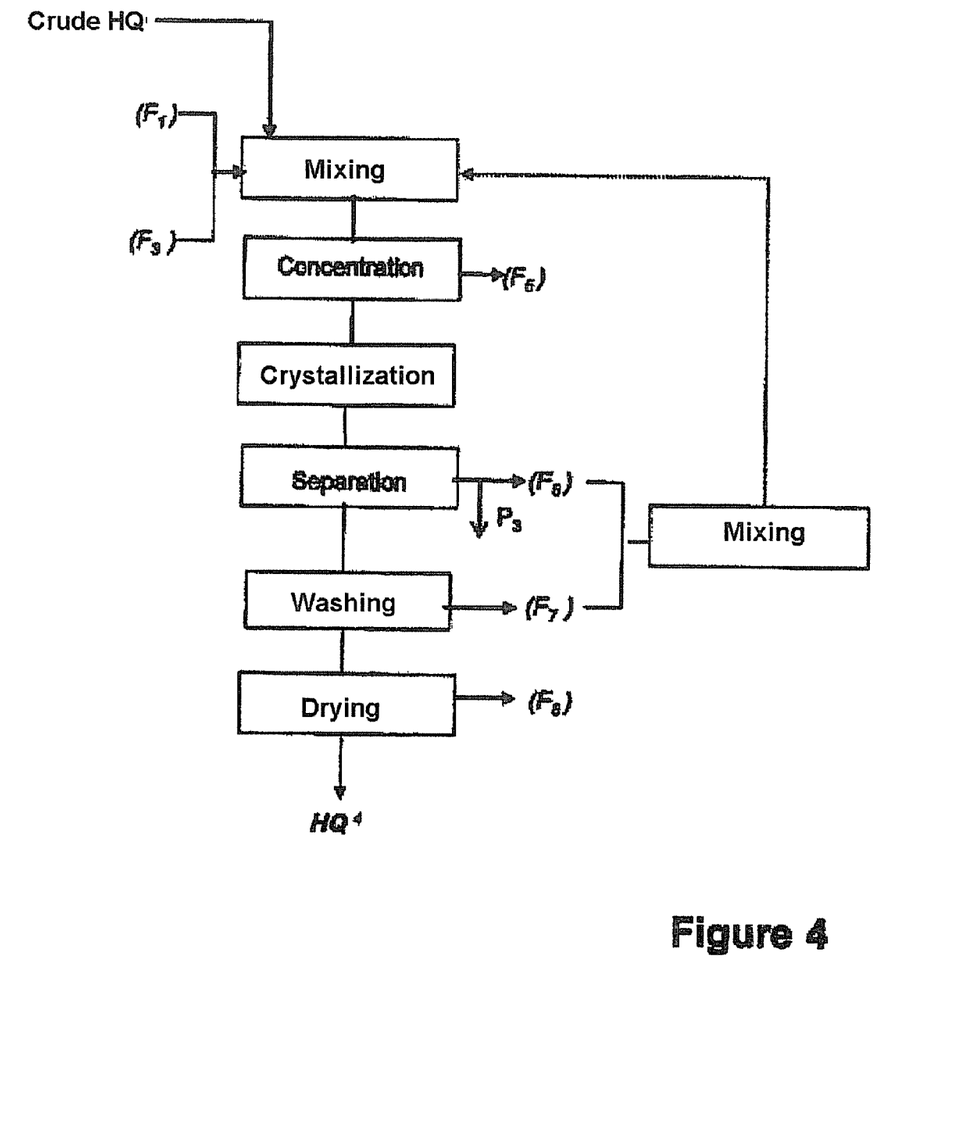
FIG. 4 illustrates steps of a fourth embodiment of a process for the purification of hydroquinones which comprises a series of steps including recycling and mixing of wash liquors and recovered stream.

Represented in FIG. 4

According to another embodiment of the invention, "technical" hydroquinone is recovered from the streams $(F_1)$ and $(F_3)$ resulting from the separation and washing operations as described above in the second embodiment.

In order to do this, use is made of a process comprising the following stages:
mixing the recovered streams $(F_1)$ and $(F_3)$ with crude hydroquinone,
concentrating the mixture obtained, resulting in the removal of a stream $(F_5)$,
crystallizing the hydroquinone present in the concentrated stream,
solid/liquid separation, making it possible to separate the crystalline hydroquinone from an aqueous phase composed of the crystallization aqueous mother liquors $(F_6)$,
washing the separated hydroquinone, making it possible to collect aqueous wash liquors $(F_7)$,
drying the washed hydroquinone with removal of water $(F_8)$,
mixing the recovered streams $(F_6)$ and $(F_7)$,
and recycling the mixture obtained to the stage of mixing the streams $(F_1)$ and $(F_3)$.

According to this alternative embodiment, the recovered streams $(F_1)$ and $(F_3)$ are mixed with crude hydroquinone.

The amount of recycled hydroquinone $(F_1)+(F_3)$ is adjusted according to the quality of the hydroquinone desired. Generally, it represents from 40 to 80% of the weight of the mixture obtained.

As described above in the scheme illustrated in FIG. 3, a bleeding is carried out at $(P_3)$ on the aqueous phase $(F_6)$ resulting from the separation of the hydroquinone recovered from the concentrated stream before mixing with the stream $(F_7)$ composed of the aqueous wash liquors.

The mixing of the recovered streams $(F_6)$ and $(F_7)$ is generally carried out at a temperature ranging from 5° C. to 70° C.

Following the various operations defined according to the scheme illustrated in FIG. 4, hydroquinone $HQ^4$ is obtained, the characteristics of which are as follows:

the hydroquinone content is greater than or equal to 99%,
the resorcinol content is less than 5000 ppm,
the pyrogallol content is less than 500 ppm,
the coloring is less than 100 Hazen.

According to the embodiment illustrated in FIG. 4, the content of hydroquinone obtained is less than or equal to 99.4% approximately.

In accordance with the process of the invention, it is possible to purify the hydroquinone obtained or capable of being obtained from a reaction mixture resulting from a hydroxylation of phenol by hydrogen peroxide in the presence of an acid catalyst, after substantial removal of the pyrocatechol by distillation, by employing a series of stages which are chosen according to the objective targeted.

Advantageously, the various operations mentioned above, dissolution, crystallization, separation, drying, and the like, are carried out under an atmosphere of inert gases, preferably under nitrogen.

It should be noted that the invention does not exclude additional stages inserted in the sequences defined by the invention, in particular the addition of normal treatment of solids, in particular a treatment with carbon black (or active charcoal) for the purpose of improving the whiteness of the product obtained.

For example, according to the schemes of FIGS. 1 to 3, it is possible to carry out this treatment before the crystallization operation and subsequent to the dissolution operation by adding an amount of carbon black or of active charcoal in a proportion of 0.02 to 0.50%, with respect to the weight of hydroquinone.

This treatment is carried out in a stirred reactor.

It is followed by a solid/liquid separation, preferably a filtration, in order to remove the carbon black, advantageously followed by a washing operation.

Another embodiment of the treatment with black is to use the fixed bed technique.

Thus, the stream resulting from the dissolution operation is conveyed over a fixed bed of carbon black, preferably in the form of granules.

The carbon black granules are placed in a column and the stream comprising the hydroquinone generally passes cocurrentwise through the fixed bed.

This technique makes it possible to economize on a separation operation.

As regards the scheme illustrated in FIG. 4, it is also possible to carry out a treatment with black as described above, before the crystallization.

Thus, the process of the invention is particularly advantageous as it makes it possible to obtain the hydroquinone with different degrees of purity ranging between at least 98% and which can be close to 100%, for example equal to 99.9%.

The lower limits of the purities achieved by the process of the invention are in the vicinity of 50 ppm for resorcinol, 50 ppm for pyrogallol and 20 ppm for pyrocatechol.

Finally, it should be emphasized that the process of the invention is advantageous from an economic viewpoint as the purification yield always remains greater than 95% by choosing the appropriate embodiment chosen from those provided by the present invention.

It should be noted that the purified hydroquinone obtained according to the process of the invention has a white appearance. The coloring of the hydroquinone is measured as specified above by spectrocolorimetry. For the hydroquinone obtained according to the invention, a colorimetric index of less than or equal to 500 Hazen and generally of greater than or equal to 5 Hazen and generally between 10 and 100 Hazen is always obtained.

It is specified that the various percentages by weight given in the present text, in relation to the hydroquinone in the solid form, are expressed with respect to a dry product obtained after drying until a constant weight is obtained.

Exemplary embodiments of the invention are given below by way of illustration and without a limiting nature.

Examples 1 to 4 refer respectively to FIGS. 1 to 4.

EXAMPLES

Example 1

2.234 kg of water, at ambient temperature, and 1.266 kg of crude hydroquinone, the composition of which in percent by weight is as follows: 97.8% of hydroquinone, 1.1% of pyrogallol and 1.1% of resorcinol, the sum of the other impurities present being less than 0.1%; respectively are run into a stirred 5 liter jacketed crystallizer equipped with a condenser which is maintained under nitrogen and at a temperature of 95° C.

Rapid cooling is carried out down to 70° C. over 30 min.

Cooling is then carried out from 70° C. to 20° C. over 5 hours at a constant rate.

The crystalline hydroquinone suspension is then filtered on a flat filter under nitrogen in order to obtain 1.369 kg of wet hydroquinone and 2.131 kg of mother liquors $(F_1)$.

The solution of mother liquors $(F_1)$ is stored for subsequent treatment.

The wet hydroquinone is dried in an oven, under reduced pressure (100 mbar) and while flushing with nitrogen, at 90° C. for 5 hours with removal of 0.254 kg of water $(F_2)$.

1.115 kg of hydroquinone $HQ^1$ are isolated, which product has the following composition by weight:

Hydroquinone content=99%
Pyrogallol content: 2300 ppm
Resorcinol content: 2500 ppm
Pyrocatechol content: 30 ppm
Water content: 0.5%
Coloring: 350 Hazen

Example 2

2.346 kg of water, at ambient temperature, and 1.330 kg of crude hydroquinone, the composition of which in percent by weight is as follows: 97.2% of hydroquinone, 1.4% of pyrogallol and 1.4% of resorcinol, the sum of the other impurities present being less than 0.2%; respectively are run into a stirred 5 liter jacketed crystallizer equipped with a condenser which is maintained under nitrogen and at a temperature of 95° C.

Rapid cooling is carried out down to 70° C. over 30 min.

Cooling is then carried out from 70° C. to 20° C. over 5 hours at a constant rate.

The crystalline hydroquinone suspension is then filtered on a flat filter under nitrogen in order to obtain 1.565 kg of wet hydroquinone and 2.111 kg of mother liquors ($F_1$) stored for subsequent treatment.

A washing operation with 0.500 kg of water is carried out on the filter at a temperature of 20° C.

0.525 kg of wash liquors ($F_3$) is recovered separately for subsequent treatment.

1.540 kg of the washed cake is dried, in an oven under reduced pressure and while flushing with nitrogen, at 90° C. for 5 hours and 0.247 kg of water ($F_4$) is evaporated.

1.293 kg of hydroquinone $HQ^2$ are isolated, which product has the following composition by weight:
Hydroquinone content=99.5%
Pyrogallol content: 70 ppm
Resorcinol content: 250 ppm
Pyrocatechol content: 20 ppm
Water content: 0.40%
Coloring: 20 Hazen Example 3

1.689 kg of mother liquors ($F_1$) from example 2, 0.525 kg of wash liquors ($F_3$) from example 2 and 0.823 kg of water, at ambient temperature, and 1.330 kg of crude hydroquinone, the composition of which in % by weight is as follows: 97.2% of hydroquinone, 1.4% of pyrogallol and 1.4% of resorcinol, the sum of the other impurities present being less than 0.2%; respectively are run into a stirred 5 liter jacketed crystallizer equipped with a condenser which is maintained under nitrogen and at a temperature of 95° C.

Rapid cooling is carried out over 30 min down to 70° C.

Cooling is then carried out over 10 hours from 70° C. to 20° C. at a constant rate.

The crystalline hydroquinone suspension is then filtered on a flat filter under nitrogen in order to obtain 1.527 kg of wet hydroquinone and 2.840 kg of mother liquors ($F_{1a}$).

Washing with 0.500 kg of water is carried out on the filter at a temperature of 20° C.

0.535 kg of wash liquors ($F_{3a}$) is recovered separately.

1.493 kg of this cake is dried in the oven, under reduced pressure and washed first with nitrogen, at 90° C. for 5 hours and 0.210 kg of water ($F_{4a}$) is evaporated.

1.283 kg of hydroquinone $HQ^3$ are isolated, which product has the following composition by weight:
HQ content=99.0%
Pyrogallol content: 110 ppm
Resorcinol content: 1600 ppm
Pyrocatechol content: 25 ppm
Water content: 0.40%
Coloring: 35 Hazen Example 4

2.346 kg of water, at ambient temperature, and 1.330 kg of crude hydroquinone, the composition of which in percent by weight is as follows: 97.2% of hydroquinone, 1.4% of pyrogallol and 1.4% of resorcinol, the sum of the other impurities present being less than 0.2%; respectively are run into a stirred 5 liter jacketed crystallizer equipped with a condenser which is maintained under nitrogen and at a temperature of 95° C.

Rapid cooling is carried out down to 70° C. over 30 min.

Cooling is then carried out from 70° C. to 20° C. over 5 hours at a constant rate.

The crystalline hydroquinone suspension is then filtered on a flat filter under nitrogen in order to obtain 1.565 kg of wet hydroquinone and 2.111 kg of mother liquors ($F_1$).

Washing with 0.500 kg of water is carried out on the filter at a temperature of 20° C.

0.525 kg of wash liquors ($F_3$) is recovered separately.

This crystallization is repeated 4 times in identical fashion.

All the streams ($F_1$) and ($F_3$) are mixed in a rotary evaporator in order to concentrate by distillation at atmospheric pressure and to obtain 2.237 kg of concentrated hydroquinone solution comprising 33% by weight after evaporating 8.307 kg of water ($F_5$).

The preceding 2.237 kg are charged to a stirred 3 liter jacketed crystallizer equipped with a condenser which is maintained under nitrogen and at a temperature of 90° C.

Rapid cooling is carried out over 20 min down to 70° C.

Cooling is then carried out over 12 hours from 70 to 20° C. at a constant rate.

The crystalline hydroquinone suspension is then filtered on a flat filter under nitrogen in order to obtain 0.710 kg of wet hydroquinone and 1.527 kg of mother liquors ($F_6$).

Washing with 0.300 kg of water is carried out on the filter at a temperature of 20° C.

0.315 kg of wash liquors ($F_7$) is recovered separately.

The sequence described below is subsequently carried out.

1.527 kg of the preceding mother liquors ($F_6$), 0.315 kg of the preceding wash liquors ($F_7$) and 0.665 kg of crude hydroquinone, the composition of which in % by weight is as follows: 97.2% of hydroquinone, 1.4% of pyrogallol and 1.4% of resorcinol, the sum of the other impurities present being less than 0.2%; respectively are run into a stirred 5 liter jacketed crystallizer equipped with a condenser which is maintained under nitrogen and at a temperature of 95° C.

In this example, all of the mother liquors ($F_6$) is used. (However, it is advantageous, in order to avoid damaging the quality, to use only a portion of the mother liquors.)

The new composition has a hydroquinone content of approximately 33% by weight.

Rapid cooling is carried out over 30 min down to 70° C.

Cooling is then carried out over 12 hours from 70° C. to 20° C. at a constant rate.

The crystalline hydroquinone suspension is then filtered on a flat filter under nitrogen in order to obtain 0.810 kg of wet hydroquinone and 1.697 kg of mother liquors ($F_6$).

Washing with 0.750 kg of water is carried out on the filter at a temperature of 20° C.

0.805 kg of wash liquors ($F_7$) and a wet hydroquinone cake of 0.755 kg are recovered separately.

0.755 kg of this cake is dried in an oven, under reduced pressure and while flushed with nitrogen, at 90° C. for 8 hours and 0.110 kg of water ($F_8$) is evaporated.

0.645 kg of hydroquinone $HQ^4$ is isolated, which product has the following composition by weight:
HQ content=99.0%
Pyrogallol content: 220 ppm
Resorcinol content: 1500 ppm
Pyrocatechol content: 25 ppm
Water content: 0.32%
Coloring: 60 Hazen It should be clearly understood that the invention defined by the appended claims is not limited to the specific embodiments indicated in the description above but encompasses the alternative forms thereof which depart neither from the scope nor from the spirit of the present invention.

Thus, the invention encompasses the embodiments which would result from the combination of the schemes defined according to FIGS. 1 to 4.

What is claimed is:
1. A process for the preparation of a purified hydroquinone from a crude hydroquinone $HQ^0$ essentially comprising hydroquinone and low amounts of impurities, including at least resorcinol, pyrogallol and trace amounts of pyrocatechol, said process comprising at least the following steps: dissolving the crude hydroquinone in water to form an aqueous solution, crystallizing the hydroquinone from the aqueous solution, obtaining purified hydroquinone by separating the crystallized hydroquinone from the aqueous solution and, optionally, drying the crystallized hydroquinone.

2. The process as defined by claim 1, comprising the following steps: dissolving the crude hydroquinone in water to form an aqueous solution, crystallizing the hydroquinone from the aqueous solution, obtaining purified hydroquinone by separating the crystallized hydroquinone from the aqueous solution and drying the crystallized hydroquinone.

3. The process as defined by claim 2, further comprising washing the crystallized hydroquinone prior to drying the crystallized hydroquinone.

4. A process for the preparation of a purified hydroquinone from a crude hydroquinone $HQ^0$ essentially comprising hydroquinone and low amounts of impurities, including at least resorcinol, pyrogallol and trace amounts of pyrocatechol, said process comprising at least the following steps:
dissolving the crude hydroquinone in water to form an aqueous solution,
crystallizing the hydroquinone from the aqueous solution,
separating the crystalline hydroquinone from an aqueous phase which comprises the crystallization aqueous mother liquors ($F_{1a}$) and forming a recovered stream comprising ($F_{1a}$),
washing the separated hydroquinone, and collecting the aqueous wash liquors as a recovered stream ($F_{3a}$),
drying the washed hydroquinone with removal of water ($F_{4a}$),
mixing the recovered stream comprising ($F_{1a}$) and the recovered stream ($F_{3a}$),
concentrating the mixture obtained from the recovered stream comprising ($F_{1a}$) and the recovered stream ($F_{3a}$) to obtain a concentrated mixture of recovered streams, and
recycling the concentrated mixture of recovered streams to the step of dissolving the crude hydroquinone in water to form an aqueous solution or to the step of crystallizing the hydroquinone from the aqueous solution.

5. The process as defined by claim 4, which further comprises a withdrawal of a portion of the concentrated mixture of recovered streams, optionally at the outlet of the concentrating region, or a withdrawal of a portion of the aqueous phase ($F_{1a}$) resulting from the separation of the hydroquinone after crystallization but prior to mixing with the stream ($F_{3a}$) composed of the aqueous wash liquors.

6. The process as defined by claim 4, which comprises the following steps:
mixing the recovered aqueous phase comprising the crystallization aqueous mother liquors ($F_{1a}$) and recovered aqueous wash liquors ($F_{3a}$) with crude hydroquinone,
concentrating the mixture obtained to form a concentrated stream comprising hydroquinone,
crystallizing the hydroquinone present in the concentrated stream,
separating the crystalline hydroquinone from an aqueous phase comprising the crystallization aqueous mother liquors ($F_6$),
washing the separated hydroquinone, and collecting aqueous wash liquors ($F_7$) as a recovered stream,
drying the washed hydroquinone with removal of water ($F_8$),
mixing the recovered streams ($F_6$) and ($F_7$), and
recycling the mixture of the recovered streams ($F_6$) and ($F_7$) into the mixture of streams ($F_{1a}$) and ($F_{3a}$).

7. The process as defined by claim 6, wherein a portion of the aqueous phase ($F_6$) resulting from the separation of the hydroquinone recovered from the concentrated stream is withdrawn prior to mixing the aqueous phase ($F_6$) with the stream ($F_7$) comprising the aqueous wash liquors.

8. The process as defined by claim 1, wherein the step of dissolving the crude hydroquinone in water is carried out by introducing an amount of water such that the concentration of the hydroquinone in the water ranges from 20% to 50% by weight.

9. The process as defined by claim 8, wherein the step of dissolving the crude hydroquinone in water is carried out at a temperature between 70° C. and 100° C.

10. The process as defined by claim 1, wherein crystallizing the hydroquinone from the aqueous solution is carried out by cooling the temperature of the aqueous solution to a temperature of from 0° C. to 40° C.

11. The process as defined by claim 1, wherein drying is performed at a temperature between 100° C. and 140° C.

12. The process as defined by claim 3, wherein the washing is carried out with an amount of water ranging from 20 to 60% of the weight of hydroquinone.

13. The process as defined by claim 4, wherein the mixing of the streams ($F_{1a}$) and ($F_{3a}$) is carried out at a temperature between 5° C. and 70° C.

14. The process as defined by claim 4, wherein the mixture of recovered streams ($F_{1a}$) and ($F_{3a}$) obtained is concentrated to increase the concentration of hydroquinone in the medium from 5% by weight to 40% by weight.

15. The process as defined by claim 14, wherein the concentrating is carried out by reducing the pressure while within the established temperature region; or by distilling at atmospheric pressure or at pressures lower than or greater than atmospheric pressure.

16. The process as defined by claim 6, wherein the mixing of the streams ($F_6$) and ($F_7$) is carried out at a temperature between 5° C. and 70° C.

17. The process as defined by claim 1, wherein the crude hydroquinone $HQ^0$ has impurities of 0.5 to 4% by weight, with respect to the total weight of the crude hydroquinone.

18. The process as defined by claim 1, wherein the crude hydroquinone $HQ^0$ comprises from 0.1 to 2% by weight of light impurities consisting essentially of resorcinol and residual pyrocatechol.

19. The process as defined by claim 1, wherein the crude hydroquinone $HQ^0$ comprises from 0.1 to 2% by weight of pyrogallol.

20. The process as defined by claim 1, wherein the crude hydroquinone $HQ^0$ comprises, by weight with respect to the total amount of crude hydroquinone:
from 96 to 99.5% of hydroquinone,
from 0.1 to 2% of resorcinol,
from 0.1 to 2% of pyrogallol, and
trace amounts of pyrocatechol.

21. The process as defined by claim 1, wherein the crude hydroquinone $HQ^0$ is obtained from a reaction mixture resulting from a hydroxylation of phenol by hydrogen peroxide in the presence of an acid catalyst, after substantial removal of the pyrocatechol by distillation.

22. The process as defined by claim 21, wherein the acid catalyst is selected from the group consisting of strong protic acids, sulfonic resins, iron(II) complexes, copper(II) complexes, and acid zeolites.

23. The process as defined by claim 2, wherein the hydroquinone obtained has the following characteristics:
the hydroquinone content is greater than or equal to 98.5%,
the resorcinol content is less than 4,000 ppm,
the pyrogallol content is less than 4,000 ppm, and
the coloring is less than 500 Hazen.

24. The process as defined by claim 3, wherein the hydroquinone obtained has the following characteristics:
the hydroquinone content is greater than or equal to 99.5%,
the resorcinol content is less than 500 ppm,
the pyrogallol content is less than 100 ppm,
the coloring is less than 30 Hazen.

25. The process as defined by claim 4, wherein the hydroquinone obtained has the following characteristics:
the hydroquinone content is greater than or equal to 99%,
the resorcinol content is less than 5,000 ppm,
the pyrogallol content is less than 200 ppm,
the coloring is less than 50 Hazen.

26. The process as defined by claim 6, wherein the hydroquinone obtained has the following characteristics:
the hydroquinone content is greater than or equal to 99%,
the resorcinol content is less than 5,000 ppm,
the pyrogallol content is less than 500 ppm,
the coloring is less than 100 Hazen.

27. The process as defined by claim 22, wherein:
(a) the strong protic acid is selected from the group consisting of sulfuric acid, a hydrochloric/sulfuric acid mixture, perchloric acid, and sulfonic acids;
(b) the sulfonic resin is selected from the group consisting of a sulfonated styrene-divinylbenzene copolymer, a phenol-formaldehyde copolymer which is substituted by a methylenesulfonic group on the aromatic ring, and a perfluorinated resin substituted by sulfonic groups; and
(c) the acid zeolite is selected from the group consisting of zeolites of titanium silicalite (titanosilicalite-1) type, iron silicalites of TS-1 type, zeolites of MEL titanium silicalite type, titanozeosilites of MFI type, and MCM-22 zeolites.

28. The process as defined by claim 27, wherein the sulfonic acid is selected from the group consisting of methanesulfonic acid, trifluoromethanesulfonic acid, toluenesulfonic acid and phenolsulfonic acid.

29. The process as defined by claim 20, wherein pyrocatechol is present at a content of less than 500 ppm (0.05%).

30. The process as defined by claim 20, wherein pyrocatechol is present at a content of less than 100 ppm (0.01%).

* * * * *